US009283167B2

(12) United States Patent
Metten et al.

(10) Patent No.: US 9,283,167 B2
(45) Date of Patent: Mar. 15, 2016

(54) USE OF A PRODUCT FOR KERATIN FIBERS, CONTAINING AT LEAST ONE SPECIFIC POLYMER COMBINATION FOR IMPROVING THE COLOR RETENTION OF OXIDATIVE HAIR COLORATIONS

(71) Applicant: Henkel AG & Co. KGaA, Duesseldorf (DE)

(72) Inventors: Diane Metten, Hamburg (DE); Bernd Richters, Hamburg (DE); Rene Scheffler, Ellerau (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/742,826

(22) Filed: Jun. 18, 2015

(65) Prior Publication Data

US 2015/0283058 A1 Oct. 8, 2015

Related U.S. Application Data

(63) Continuation of application No. PCT/EP2013/074433, filed on Nov. 22, 2013.

(30) Foreign Application Priority Data

Dec. 20, 2012 (DE) .......................... 10 2012 224 051

(51) Int. Cl.
*A61Q 5/10* (2006.01)
*A61K 8/81* (2006.01)
*A61Q 5/00* (2006.01)

(52) U.S. Cl.
CPC ............. *A61K 8/8164* (2013.01); *A61K 8/8158* (2013.01); *A61Q 5/004* (2013.01); *A61Q 5/10* (2013.01); *A61K 2800/4324* (2013.01); *A61K 2800/594* (2013.01)

(58) Field of Classification Search
CPC ....... A61Q 5/10; A61Q 5/004; A61K 8/8164; A61K 8/8158; A61K 2800/594; A61K 2800/4324
USPC ............................................................ 8/405
See application file for complete search history.

(56) References Cited

U.S. PATENT DOCUMENTS

| 6,235,913 | B1 | 5/2001 | Raths et al. | |
|---|---|---|---|---|
| 7,332,466 | B2 | 2/2008 | Schmid et al. | |
| 7,713,310 | B2 | 5/2010 | Lalleman | |
| 9,072,685 | B2 * | 7/2015 | Metten | A61Q 5/06 |
| 2010/0147319 | A1 | 6/2010 | Lalleman | |
| 2010/0147320 | A1 | 6/2010 | Lalleman | |
| 2011/0219552 | A1 | 9/2011 | Zhou et al. | |

FOREIGN PATENT DOCUMENTS

| EP | 0998908 | A2 | 5/2000 | |
|---|---|---|---|---|
| EP | 1915981 | B1 | 4/2010 | |
| WO | 2012/075274 | A1 | 6/2012 | |
| WO | 2012/084877 | A2 | 6/2012 | |
| WO | WO2013/056888 | A2 * | 4/2013 | A61K 8/00 |

OTHER PUBLICATIONS

PCT International Search Report (PCT/EP2013/074433) dated Oct. 22, 2014.
Database GNPD [Online] MINTEL, "The Power of Now .in Color Elasticity Color Infusion", XP002723958, Database accession No. 1429238, Oct. 2010.

* cited by examiner

*Primary Examiner* — Eisa Elhilo
(74) *Attorney, Agent, or Firm* — P. Scott Smith

(57) ABSTRACT

Methods and related agents. Said agents including, in a cosmetically acceptable carrier, a) at least one copolymer A having at least one structural unit (A1), at least one structural unit (A2), at least one structural unit (A3) and at least one structural unit (A4), wherein R1 represents an optionally heterofunctionalized alkyl group; R2 represents an optionally heterofunctionalized alkyl group which is different from R1; R3 independently represents an optionally heterofunctionalized alkyl group different from R1 and R2, and b) at least one copolymer B, which is different from copolymer A and has at least one structural unit (B1), wherein R4 represents an optionally heterofunctionalized alkyl group, improve the color retention of oxidatively dyed keratin-containing fibers.

20 Claims, No Drawings

USE OF A PRODUCT FOR KERATIN FIBERS, CONTAINING AT LEAST ONE SPECIFIC POLYMER COMBINATION FOR IMPROVING THE COLOR RETENTION OF OXIDATIVE HAIR COLORATIONS

FIELD OF THE INVENTION

The present invention generally relates to the use of an agent for hair treatment, containing a combination of at least one nonionic starch that is modified by propylene oxide, with at least one film-forming and/or fixing anionic polymer for improving the color retention of oxidative hair colorations, and corresponding methods for treating keratin-containing fibers.

BACKGROUND OF THE INVENTION

Keratin-containing fibers are understood in principle to mean all animal hair, for example wool, horsehair, Angora hair, fur, feathers, and products or textiles manufactured therefrom. However, the keratinic fibers are preferably human hair.

The dyeing of keratinic fibers, for example human keratin fibers, generally takes place using coloring compositions which, in addition to other components, contain oxidation dye precursors, in particular oxidation bases ("developers"). After addition of an oxidizing agent as part of an oxidative condensation, these colorless or weakly colored substances react to form dye molecules. For shading the colors thus obtained, a second group of oxidation dye precursors, the so-called couplers, are generally added to the developers. A large number of different tints can be achieved by combining developer and coupler components.

In addition or as an alternative to the above-mentioned oxidation dyes, keratin fibers are dyed by means of direct dyes. These direct dyes are colored molecules that attach to the surface of the keratin fibers.

The coloration of the keratinic fiber obtained by oxidation dyes or direct dyes fades due to external influences such as light, but in particular due to repeated hair washing.

To improve the color retention of oxidatively dyed keratin fibers, the use of zinc salts, for example, is proposed in European Patents EP 1 915 981 B1 and EP 1 923 042 B1. According to the teaching of these documents, the zinc salts are applied to the keratinic fibers after completion of the dyeing process.

However, the color retention values achieved according to the teaching of these documents are not satisfactory in every case.

In summary, there is therefore still a need for methods for improving the color retention of dyed keratinic fibers. Against this background, it has been determined that improved color retention can be achieved by treating keratinic fibers with a combination of specific polymers.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

Use of an agent which contains in a cosmetically acceptable carrier: a) at least one copolymer A having at least one structural unit (A1), at least one structural unit (A2), at least one structural unit (A3), and at least one structural unit (A4)

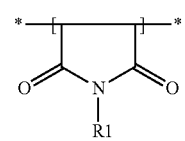
(A1)

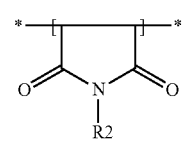
(A2)

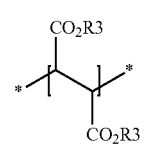
(A3)

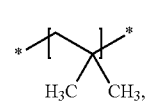
(A4)

Wherein R1 stands for an optionally heterofunctionalized alkyl radical, R2 stands for an optionally heterofunctionalized alkyl radical which is different from R1, R3 independently stands for an optionally heterofunctionalized alkyl radical which is different from R1 and R2; and b) at least one copolymer B, which is different from copolymer A, having at least one structural unit (B1)

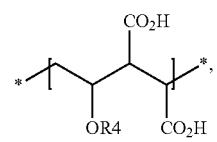
(B1)

wherein R4 stands for an optionally heterofunctionalized alkyl radical, for improving the color retention of oxidatively dyed keratin-containing fibers, in particular of oxidatively dyed human hair.

Method for treating keratin-containing fibers, in particular human hair, comprising the following steps: i) carrying out oxidative dyeing of the keratin-containing fiber; and ii) applying an agent which contains in a cosmetically acceptable carrier a) at least one copolymer A comprising at least one structural unit (A1), at least one structural unit (A2), at least one structural unit (A3), and at least one structural unit (A4)

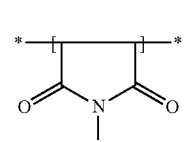
(A1)

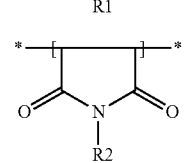
(A2)

-continued

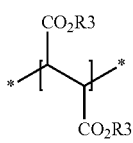
(A3)

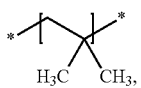
(A4)

wherein R1 stands for an optionally heterofunctionalized alkyl radical, R2 stands for an optionally heterofunctionalized alkyl radical which is different from R1, and R3 independently stands for an optionally heterofunctionalized alkyl radical which is different from R1 and R2; and b) at least one copolymer B, which is different from copolymer A, having at least one structural unit (B1)

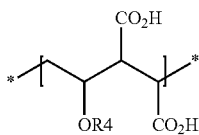
(B1)

wherein R4 stands for an optionally heterofunctionalized alkyl radical, to the oxidatively dyed keratin-containing fiber.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

A first subject matter of the present invention relates to the use of an agent which contains in a cosmetically acceptable carrier a) at least one copolymer A having at least one structural unit (A1), at least one structural unit (A2), at least one structural unit (A3), and at least one structural unit (A4)

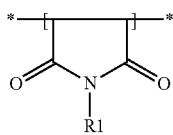
(A1)

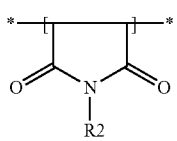
(A2)

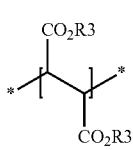
(A3)

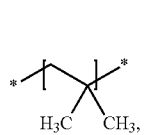
(A4)

wherein
R1 stands for an optionally heterofunctionalized alkyl radical;
R2 stands for an optionally heterofunctionalized alkyl radical which is different from R1;
R3 independently stands for an optionally heterofunctionalized alkyl radical which is different from R1 and R2;
b) at least one copolymer B, which is different from copolymer A, having at least one structural unit (B1)

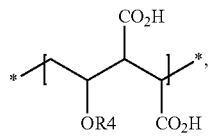
(B1)

wherein R4 stands for an optionally heterofunctionalized alkyl radical,
for improving the color retention of oxidatively dyed keratin-containing fibers, in particular of oxidatively dyed human hair.

According to the above formulas and all the formulas below, a chemical bond that is denoted by the symbol "*" stands for a free valence of the corresponding structural fragment.

According to the invention, the improvement of the color retention encompasses the retention of the color under the action of external influences. The color retention thus encompasses, for example, phenomena such as wash fastness, light fastness, rubbing fastness, or perspiration fastness of the oxidative hair coloring. The use according to the invention has particular advantages with regard to the color retention after washing the keratin fibers. The use of compositions according to the invention for improving the wash fastness of oxidatively dyed keratin-containing fibers, in particular of oxidatively dyed human hair, is therefore a preferred embodiment of the present patent application.

The agents according to the invention contain the active substances in a cosmetic carrier. This cosmetic carrier is aqueous, alcoholic, or aqueous-alcoholic. Within the meaning of the present invention, aqueous-alcoholic carriers are understood to mean water-containing compositions which contain 3 to 70% by weight of a $C_1$-$C_4$ alcohol, in particular ethanol or isopropanol, based on the total weight of the application mixture. Within the meaning of the invention, an aqueous carrier contains at least 30% by weight, in particular at least 50% by weight, of water, based on the total weight of the application mixture. Preferred cosmetic agents contain 40 to 99% by weight, preferably 50 to 98% by weight, particularly preferably 60 to 95% by weight, and in particular 70 to 90% by weight, of water, based on the total weight of the cosmetic agent.

The agents according to the invention contain as the first important component a copolymer A, comprising the structural units (A1), (A2), (A3), and (A4). For the technical effect of the agents according to the invention, it has proven to be advantageous when copolymer A is composed of at least 70% by weight, preferably at least 80% by weight, more preferably at least 90% by weight, and in particular at least 95% by weight, of the structural units (A1), (A2), (A3), and (A4). Further preferred copolymers A are composed completely of the structural units (A1), (A2), (A3), and (A4).

In one preferred embodiment, the radical R1 in the structural unit (A1) stands for an ether radical, preferably for a polyalkoxylated radical. Structural units (A1) in which R1 in formula (A1) stands for a —CH(CH$_3$)CH$_2$—(OCH(CH$_3$)CH$_2$)$_x$(O[CH$_2$]$_2$)$_y$OCH$_3$ radical, in which x and y independently of one another have a value between 1 and 100, are particularly preferred.

The radical R2 in the structural unit (A2) preferably stands for a radical containing an amino group, preferably for a radical containing a tertiary amine. Structural units (A2) in which R2 in formula (A2) stands for a —(CH$_2$)$_3$—N(CH$_3$)$_2$ radical are particularly preferred.

In the structural unit (A3), at least one of the radicals R3 preferably stands for at least one alkyl radical, preferably a (C1 to C4) alkyl radical. Structural units (A3) in which R3 stands for —CH$_2$CH$_3$ or —CH$_2$CH$_2$CH$_3$, preferably for —CH$_2$CH$_3$, and a radical R3 in formula (A3) stands for H, are particularly preferred.

Several preferred copolymers A are listed below. These copolymers A are composed of at least 70% by weight, preferably at least 80% by weight, more preferably at least 90% by weight, and in particular at least 95% by weight, particularly preferably completely, of the structural units (A1), (A2), (A3), and (A4):

A-I) Copolymer A having at least one structural unit (A1), at least one structural unit (A2), at least one structural unit (A3), and at least one structural unit (A4),

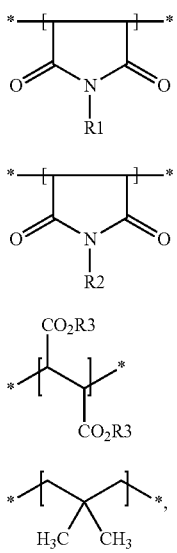

wherein
R1 in formula (A1) stands for a —CH(CH$_3$)CH$_2$—(OCH(CH$_3$)CH$_2$)$_x$(O[CH$_2$]$_2$)$_y$OCH$_3$ radical in which x and y independently of one another have a value between 1 and 100;
R2 in formula (A2) stands for a —(CH$_2$)$_3$—N(CH$_3$)$_2$ radical;
R3 independently stands for an optionally heterofunctionalized alkyl radical which is different from R1 and R2.

A-II) Copolymer A having at least one structural unit (A1), at least one structural unit (A2), at least one structural unit (A3), and at least one structural unit (A4),

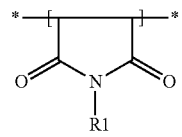

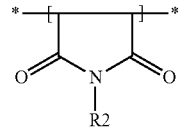

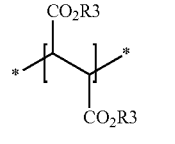

wherein
R1 in formula (A1) stands for a —CH(CH$_3$)CH$_2$—(OCH(CH$_3$)CH$_2$)$_x$(O[CH$_2$]$_2$)$_y$OCH$_3$ radical, in which x and y independently of one another have a value between 1 and 100;
R2 stands for an optionally heterofunctionalized alkyl radical which is different from R1;
a radical R3 in formula (A3) stands for —CH$_2$CH$_3$ or —CH$_2$CH$_2$CH$_3$, preferably for —CH$_2$CH$_3$, and a radical R3 in formula (A3) stands for H.

A-III) Copolymer A having at least one structural unit (A1), at least one structural unit (A2), at least one structural unit (A3), and at least one structural unit (A4),

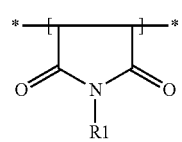

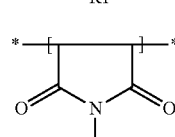

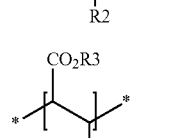

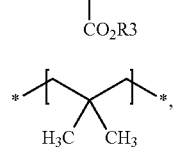

wherein
R1 stands for an optionally heterofunctionalized alkyl radical;
R2 in formula (A2) stands for a —(CH$_2$)$_3$—N(CH$_3$)$_2$ radical;

a radical R3 in formula (A3) stands for —CH$_2$CH$_3$ or —CH$_2$CH$_2$CH$_3$, preferably for —CH$_2$CH$_3$, and a radical R3 in formula (A3) stands for H.

Cosmetic agents according to the invention which are very particularly preferred are characterized in that the radical R1 in formula (A1) stands for a —CH(CH$_3$)CH$_2$—(OCH(CH$_3$)CH$_2$)$_x$(O[CH$_2$]$_2$)$_y$OCH$_3$ radical, in which x and y independently of one another have a value between 1 and 100;

the radical R2 in formula (A2) stands for a —(CH$_2$)$_3$—N(CH$_3$)$_2$ radical;

a radical R3 stands for —CH$_2$CH$_3$, and a radical R3 in formula (A3) stands for H.

The weight fraction of copolymer A relative to the total weight of cosmetic agents according to the invention is preferably 0.05 to 10% by weight, preferably 0.1 to 7.0% by weight, and in particular 0.2 to 5.0% by weight.

As the second important component, the agents according to the invention contain a copolymer B, comprising the structural unit (B1). For the technical effect of the agents according to the invention, it has proven to be advantageous when copolymer B is composed of at least 70% by weight, preferably at least 80% by weight, more preferably at least 90% by weight, and in particular at least 95% by weight, of structural unit (B1). Further preferred copolymers B are composed completely of structural unit (B1).

In one preferred embodiment, the radical R4 in structural unit (B1) stands for an alkyl radical, preferably a C1 to C4 alkyl radical. The structural unit (B1) in which the radical R4 stands for —CH$_3$ is particularly preferred.

The weight fraction of copolymer B relative to the total weight of cosmetic agents according to the invention is preferably 0.05 to 10% by weight, preferably 0.1 to 7.0% by weight, and in particular 0.2 to 5.0% by weight.

A cosmetic agent which is preferably used according to the invention is characterized in that the total quantity of the mixture of copolymer A and copolymer B is 0.1 to 10.0% by weight, in particular 1.0 to 5.0% by weight, based on the total weight of the agent.

Copolymers A and B may be incorporated into the agent according to the invention in pure form. However, for the processing and the cosmetic properties of the cosmetic agents according to the invention, it has proven to be advantageous to use copolymers A and B in pre-prepared form, i.e., in combination with further active substances or auxiliary substances. In particular mixtures of copolymers A and B are used. The weight ratio of copolymer A to copolymer B in preferably used polymer mixtures is 20:1 to 1:20, preferably 10:1 to 1:10, in particular 8:1 to 1:8, and very particularly preferably 5:1 to 1:5. Consequently, cosmetic agents according to the invention are also preferred in which the weight ratio of copolymer A to copolymer B is 20:1 to 1:20, preferably 10:1 to 1:10, in particular 8:1 to 1:8, and very particularly preferably 5:1 to 1:5. The use of copolymers A and B in a weight ratio of 2:1 to 1:4, preferably 1:1 to 1:3, is very particularly preferred. Copolymer B is preferably used in excess.

The above-described copolymers A and B or the mixtures thereof are preferably combined with additional auxiliary substances. The use of alcohols is particularly preferred. A preferred class of alcohols is diols, in particular 1,2-diols. 1,2-Octanediol is particularly preferably used. In particular 1,2-octanediol not only simplifies the further processing of copolymers A and B or the mixtures thereof, but also further intensifies their advantageous technical effect, in particular their care effect.

The above-mentioned diols may be incorporated into the cosmetic agents according to the invention either together with copolymers A and B or a mixture thereof, or separately from copolymers A and B. Against this background, cosmetic agents according to the invention are preferred which additionally contain at least one 1,2-diol, preferably 1,2-octanediol.

A polymer mixture which is based on copolymers A and B and preferred according to the invention is marketed by ISP under the name Styleze® XT3 (INCI: Water (and) Polyimide-1 (and) PVM/MA Copolymer (and) Caprylyl Glycol (proposed)).

The cosmetic agents used according to the invention may additionally contain at least one further fixing polymer which is different from copolymers A and B.

Fixing polymers contribute to the hold and/or to the establishment of volume and fullness of the hair in the overall hairstyle. At the same time, these polymers are also film-forming polymers, and therefore are generally typical substances for hair treatment agents used for shaping, such as hair setting agents, hair foams, hair waxes, and hairsprays. The film formation may be entirely localized, and may bond only a few fibers together.

The so-called three-point bending test or curl retention test is frequently used as a test method for the fixing effect of a polymer.

Film-forming polymers are understood to mean polymers which leave behind a continuous film on the skin, the hair, or the nails upon drying. These types of film formers may be used in a wide range of cosmetic products such as face masks, makeup, hair setting agents, hairsprays, hair gels, hair waxes, hair masks, shampoos, or nail polishes. Polymers are particularly preferred which have sufficient solubility in water or water/alcohol mixtures in order to be present in the agent according to the invention in completely dissolved form. The film-forming polymers may be of synthetic or natural origin.

According to the invention, film-forming polymers are also understood to mean polymers which, when used in a 0.01 to 20% by weight aqueous, alcoholic, or aqueous-alcoholic solution, are capable of depositing a transparent polymer film on the hair.

The properties of the agent according to the invention have proven to be particularly advantageous when it is provided as an aerosol spray, aerosol foam, pump spray, or pump foam. This preferred form of preparation is described in detail below.

Particularly preferred film-forming and/or fixing polymers are anionic. According to the invention, an anionic polymer is understood to mean a polymer which in a protic solvent at standard conditions bears structural units having anionic groups, which can be compensated for by counterions to maintain electroneutrality, and contains no structural units having permanent cationic groups. Carboxylic acid groups and sulfonic acid groups fall under anionic groups.

Film-forming anionic and/or fixing anionic polymers which comprise at least one structural unit of formula (I) and at least one structural unit of formula (II)

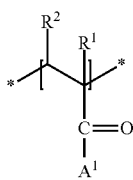

(I)

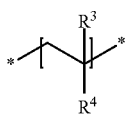

(II)

have been found to be particularly effective,
wherein
$R^1$ and $R^2$ independently stand for a hydrogen atom or a methyl group, with the condition that $R^1$ and $R^2$ do not simultaneously stand for a methyl group,
$R^3$ stands for a hydrogen atom or a methyl group,
$R^4$ stands for a carbamoyl group, a linear or branched ($C_4$ to $C_{12}$) alkylaminocarbonyl group, a linear or branched ($C_4$ to $C_{12}$) alkylaminoethylaminocarbonyl group, a linear or branched ($C_4$ to $C_{12}$) alkylaminopropylaminocarbonyl group, a linear or branched ($C_4$ to $C_{12}$) alkyloxycarbonyl group, a linear or branched ($C_4$ to $C_{12}$) alkylaminoethyloxycarbonyl group, a linear or branched ($C_4$ to $C_{12}$) alkylaminopropyloxycarbonyl group, or a linear or branched ($C_2$ to $C_{12}$) acyloxy group,
$A^1$ stands for a hydroxy group or an organic radical which has at least one sulfonic acid group and bonds to the structural fragment via an oxygen atom or an NH group.

The additional fixing polymers are preferably included in the agent used according to the invention in a quantity of 0.5% by weight to 10% by weight, particularly preferably 1.0% by weight to 9.0% by weight, very particularly preferably 3.0% by weight to 8.0% by weight, in each case based on the weight of the agent used according to the invention.

It is preferred according to the invention when the additional fixing anionic polymer includes at least one structural unit of formula (I), which is selected from at least one structural unit of formulas (I-1) to (I-5)

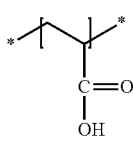

(I-1)

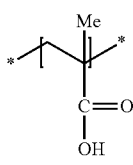

(I-2)

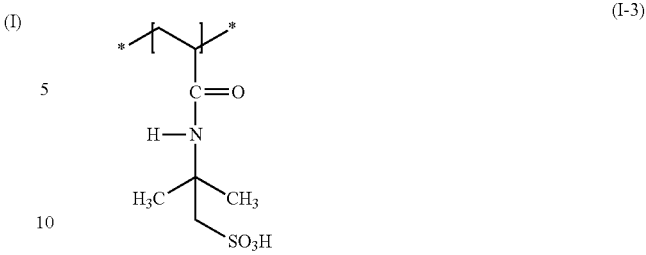

(I-3)

(I-4)

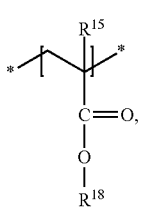

(I-5)

In this case, it is further particularly preferred when the additional fixing polymer includes, in addition to the above structural units of formulas (I) and (II), at least one structural unit of formula (III)

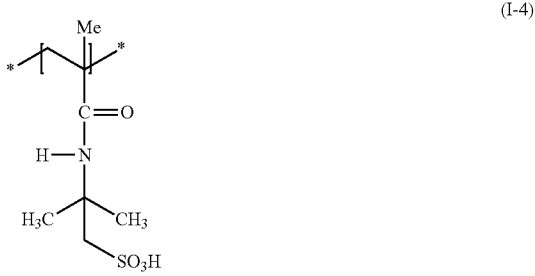

(III)

wherein
$R^{15}$ stands for a hydrogen atom or a methyl group,
$R^{16}$ stands for a ($C_1$ to $C_4$) alkyl group, in particular a methyl group or an ethyl group.

Copolymers of methacrylic acid and ethyl acrylate and tert-butyl acrylate, for example, are preferably suitable.

It is particularly preferred according to the invention when the additional fixing anionic polymer includes at least one structural unit of formula (II) which is selected from at least one structural unit of formulas (II-1) to (II-15)

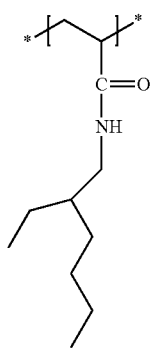 (II-1)
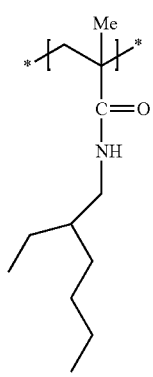 (II-2)
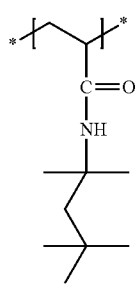 (II-3)
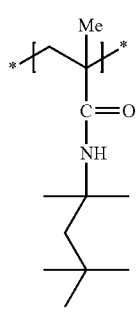 (II-4)
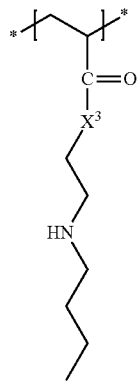 (II-5)
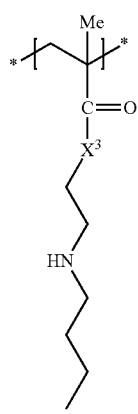 (II-6)
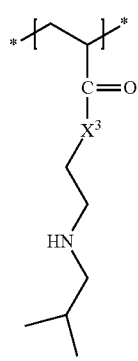 (II-7)
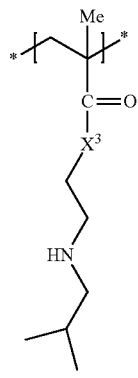 (II-8)

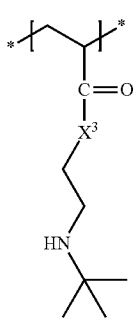
(II-9)

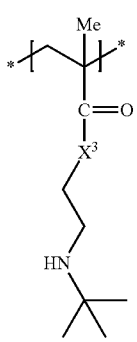
(II-10)

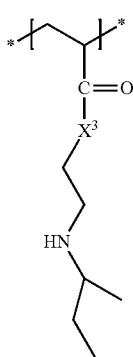
(II-11)

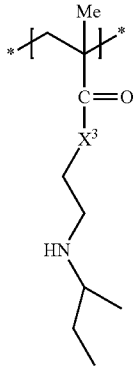
(II-12)

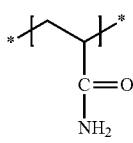
(II-13)

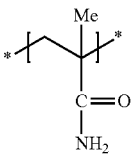
(II-14)

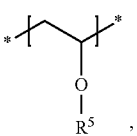
(II-15)

wherein $X^3$ stands for an oxygen atom or an NH group, $R^5$ stands for a ($C_2$ to $C_{12}$) acyl group, in particular for acetyl or neodecanoyl.

It is preferred according to the invention when $X^3$ according to formulas (II-5) to (II-12) stands for an oxygen atom.

Within the scope of a first preferred embodiment of the invention, the agent used according to the invention includes at least one additional fixing anionic polymer which comprises at least one structural unit of formula (I-1), at least one structural unit of formula (II-3), and at least one structural unit of formula (II-16), in particular selected from the group comprising formulas (II-5) to (II-12) above, with the condition that $X^3$ stands for an oxygen atom,

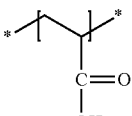
(I-1)

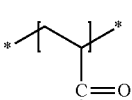
(II-3)

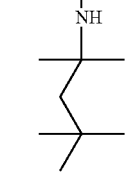

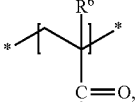
(II-16)

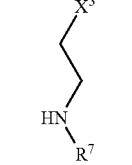

wherein $X^3$ stands for an oxygen atom or an NH group, $R^6$ stands for a hydrogen atom or a methyl group, and $R^7$ stands for an alkyl group including 4 carbon atoms, in particular n-butyl, sec-butyl, isobutyl, or tert-butyl.

In this case, it is further particularly preferred when the additional fixing polymer includes, in addition to the above structural units of formulas (I-1), (II-3), and (II-16), at least one structural unit of formula (III)

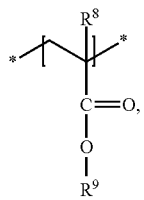
(III)

wherein
$R^8$ stands for a hydrogen atom or a methyl group, and
$R^9$ stands for a ($C_1$ to $C_4$) alkyl group, in particular a methyl group or an ethyl group.

Preferred additional fixing polymers of this type are selected from the group comprising:
  copolymers of acrylic acid, ($C_1$ to $C_4$) alkyl acrylates, $C_4$ alkylaminoethyl methacrylate, and $C_8$ alkyl acrylamide.

One example of a polymer which is particularly preferably usable within the scope of this embodiment is the polymer obtainable from National Starch under the trade name Amphomer® 028-4910, having the INCI name Octylacrylamide/Acrylates/Butylaminoethylmethacrylate Copolymer.

Within the scope of a further embodiment, agents are preferred according to the invention which as an additional anionic fixing polymer include at least one polymer which includes at least one structural unit of formula (I-3) and at least one structural unit of formula (II-13)

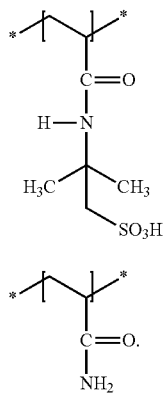
(I-3)

(II-13)

Preferred polymers of this type are selected from at least one polymer of the group comprising
  copolymers of 2-acrylamido-2-methylpropanesulfonic acid and acrylamide,
  copolymers of 2-acrylamido-2-methylpropanesulfonic acid, acrylamide, and acrylic acid.

Polymers of this type are marketed, for example, in an invert isohexadecane emulsion by Seppic under the trade name Sepigel® 305 (INCI name: Polyacrylamide, C13-14 Isoparaffin, Laureth-7) or Simulgel® 600 (INCI name: Acrylamide/Acryloyl Dimethyl Taurate Copolymer, Isohexadecane, Polysorbate-80).

An agent that is particularly preferably used according to the invention is characterized in that it includes a copolymer (b1) as the polymer.

These copolymers (b1) may be described by the general formula

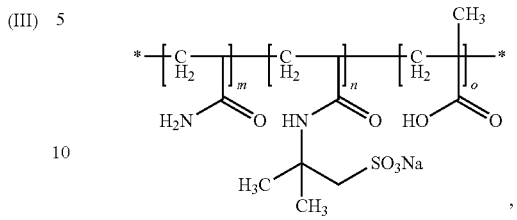

wherein the indices m, n, and o vary depending on the molar mass of the polymer, and are not to intended to mean that these are block copolymers. Rather, structural units may be present in the molecule in a statistical distribution.

Agents that are particularly preferably used according to the invention are characterized in that copolymer (b1) has a molar mass of 50 to 500 kDa, preferably 100 to 450 kDa, more preferably 150 to 400 kDa, and in particular 200 to 300 kDa.

Copolymers of acrylamide with methacrylic acid and acryloyl dimethyl taurate are obtainable, for example, under the trade name Acudyne® SCP (Rohm & Haas).

Within the scope of another embodiment, agents which as additional anionic fixing polymer include at least one polymer which includes at least one structural unit of formula (I-5) and at least one structural unit of formula (II-15)

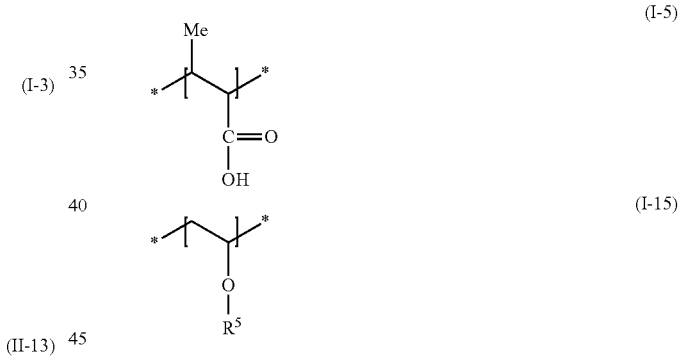
(I-5)

(I-15)

are considered to be preferred according to the invention, wherein $R^5$ stands for a ($C_2$ to $C_{12}$) acyl group, in particular for acetyl or neodecanoyl. Particularly preferred polymers of this type are selected from at least one polymer of the group comprising
  copolymers of vinyl acetate and crotonic acid,
  copolymers of vinyl propionate and crotonic acid,
  copolymers of vinyl neodecanoate, vinyl acetate, and crotonic acid.

Such copolymers are provided, for example, by Clariant under the trade name Aristoflex A 60 (INCI name: VA/Crotonates Copolymer) in an isopropanol-water mixture (60% by weight active substance), by BASF under the trade name Luviset CA 66 (vinyl acetate/crotonic acid copolymer 90:10, INCI name VA/Crotonates Copolymer), and by National Starch under the trade names Resyn 28-2942 and Resyn 28-2930 (INCI name: VA/Crotonates/Vinyl Neodecanoate Copolymer).

Within the scope of these embodiments, the above-mentioned preferred embodiments of copolymers A and B are preferably suited (see above).

All of the above-mentioned preferred quantity statements with regard to copolymers A and B for use of the agent according to the invention are similarly considered, mutatis mutandis, to be preferred also for these embodiments.

The agents used according to the invention may be formulated in all customary forms for hair care agents, for example in the form of solutions which may be applied to the hair as hair tonic or a pump spray or aerosol spray, in the form of creams, emulsions, waxes, gels, or surfactant-containing foaming solutions, or other preparations that are suitable for application to the hair. The agents according to the invention are preferably designed as a cream or gel or pump foam or aerosol foam. In particular, the cosmetic carrier is present in the form of a cream, a gel, or a foam.

According to the invention, a cream is understood to mean a composition in the form of a dispersed system which in addition to water includes fat and/or oil. Preferred suitable fats and oils are described in the present patent application (see below).

According to the invention, a gel is understood to mean a dimensionally stable, easily deformable, dispersed system which consists of a colloidally dispersed substance having long or highly branched particles, and a liquid as a dispersing agent. Polymeric thickeners are preferably used as long or highly branched particles (see below).

According to the invention, a foam is understood to mean a dispersed system in which a gas as the dispersed phase is present in a liquid as the continuous phase.

For intensifying the effect according to the invention, the agents according to the invention preferably additionally include at least one surfactant, wherein nonionic, anionic, cationic, and ampholytic surfactants are suitable in principle. The group of ampholytic or also amphoteric surfactants includes zwitterionic surfactants and ampholytes. According to the invention, the surfactants may already have an emulsifying effect.

The additional surfactants are preferably included in the agent used according to the invention in a quantity of 0.01% by weight to 5% by weight, particularly preferably 0.05% by weight to 0.5% by weight, in each case based on the weight of the agent.

It has proven to be particularly preferable when the agents used according to the invention additionally include at least one nonionic surfactant.

As a hydrophilic group, nonionic surfactants include, for example, a polyol group, a polyalkylene glycol ether group, or a combination of a polyol group and a polyglycol ether group. Examples of such compounds are the following:

addition products of 2 to 100 mol ethylene oxide and/or 1 to 5 mol propylene oxide with linear and branched fatty alcohols containing 8 to 30 C atoms, with fatty acids containing 8 to 30 C atoms, and with alkylphenols containing 8 to 15 C atoms in the alkyl group, addition products, closed with a methyl or $C_2$-$C_6$ alkyl radical end group, of 2 to 50 mol ethylene oxide and/or 1 to 5 mol propylene oxide with linear and branched fatty alcohols containing 8 to 30 C atoms, with fatty acids containing 8 to 30 C atoms, and with alkylphenols containing 8 to 15 C atoms in the alkyl group, such as the types obtainable under the trade names Dehydol® LS and Dehydol® LT (Cognis), $C_{12}$-$C_{30}$ fatty acid mono- and diesters of addition products of 1 to 30 mol ethylene oxide with glycerin, addition products of 5 to 60 mol ethylene oxide with castor oil and hydrogenated castor oil, polyol fatty acid esters, such as the commercial product Hydagen® HSP (Cognis) or Sovermol types (Cognis), alkoxylated triglycerides,
alkoxylated fatty acid alkyl esters of formula (E4-I)

$$R^1CO\text{---}(OCH_2CHR^2)_w OR^3 \tag{E4-I}$$

in which $R^1CO$ stands for a linear or branched, saturated and/or unsaturated acyl radical containing 6 to 22 carbon atoms, $R^2$ stands for hydrogen or methyl, $R^3$ stands for linear or branched alkyl radicals containing 1 to 4 carbon atoms, and w stands for numbers from 1 to 20, aminoxides,
hydroxy mixed ethers as described in German Unexamined Patent Application 19738866, for example,
sorbitan fatty acid esters and addition products of ethylene oxide with sorbitan fatty acid esters, for example polysorbates,
sugar fatty acid esters and addition products of ethylene oxide with sugar fatty acid esters,
addition products of ethylene oxide with fatty acid alkanolamides and fatty amines,
sugar surfactants of the alkyl oligoglycoside and alkenyl oligoglycoside type according to formula (E4-II)

$$R^4O\text{-}[G]_p \tag{E4-II}$$

in which $R^4$ stands for an alkyl or alkenyl radical containing 4 to 22 carbon atoms, G stands for a sugar radical containing 5 or 6 carbon atoms, and p stands for numbers from 1 to 10. The sugar surfactants may be obtained according to appropriate methods in preparative organic chemistry.

The alkylene oxide addition products with saturated linear fatty alcohols and fatty acids, in each case containing 2 to 100 mol ethylene oxide per mol fatty alcohol or fatty acid, have proven to be very particularly preferred nonionic surfactants. Preparations having excellent properties are likewise obtained when they include $C_{12}$-$C_{30}$ fatty acid mono- and diesters of addition products of 1 to 30 mol ethylene oxide with glycerin, and/or addition products of 5 to 60 mol ethylene oxide with castor oil and hydrogenated castor oil as nonionic surfactants.

The agents according to the invention very particularly preferably include as surfactant at least one addition product of 15 to 100 mol ethylene oxide, in particular 15 to 50 mol ethylene oxide, with a linear or branched (in particular linear) fatty alcohol containing 8 to 22 carbon atoms. These are very particularly preferably ceteareth-15, ceteareth-25, or ceteareth-50, which are marketed as Eumulgin® CS 15 (COGNIS), Cremophor A25 (BASF SE), and Eumulgin® CS 50 (COGNIS), respectively.

In principle, all anionic surface-active substances that are suitable for use on the human body are suited as anionic surfactants. These are characterized by a water-solubilizing anionic group such as a carboxylate, sulfate, sulfonate, or phosphate group, and a lipophilic alkyl group containing approximately 8 to 30 C atoms. In addition, glycol ether or polyglycol ether groups, ester, ether, and amide groups, and hydroxyl groups may be included in the molecule. Examples of suitable anionic surfactants, in each case in the form of the sodium, potassium, and ammonium salts, and the mono-, di-, and trialkanolammonium salts including 2 to 4 C atoms in the alkanol group, are the following:

linear and branched fatty acids having 8 to 30 C atoms (soaps),
ether carboxylic acids of formula R—O—$(CH_2$—$CH_2O)_x$ $CH_2$—COOH, in which R is a linear alkyl group having 8 to 30 C atoms, and x=0 or 1 to 16,
acyl sarcosides having 8 to 24 C atoms in the acyl group,
acyl taurides having 8 to 24 C atoms in the acyl group, acyl isethionates having 8 to 24 C atoms in the acyl group,
sulfosuccinic acid mono- and dialkyl esters having 8 to 24
 C atoms in the alkyl group, and sulfosuccinic acid
 monoalkylpolyoxyethyl esters having 8 to 24 C atoms in
 the alkyl group and 1 to 6 oxyethyl groups,
linear alkane sulfonates having 8 to 24 C atoms,
linear alpha-olefin sulfonates having 8 to 24 C atoms,
alpha-sulfofatty acid methyl esters of fatty acids having 8
 to 30 C atoms,
alkyl sulfates and alkyl polyglycol ether sulfates of formula R—O(CH$_2$—CH$_2$O)$_x$OSO$_3$H, in which R is a preferably linear alkyl group having 8 to 30 C atoms, and x=0 or 1 to 12,
mixtures of surface-active hydroxysulfonates,
sulfated hydroxyalkyl polyethylene ethers and/or hydroxyalkylene propylene glycol ethers,
Sulfonates of unsaturated fatty acids having 8 to 24 C atoms and 1 to 6 double bonds,
esters of tartaric acid and citric acid with alcohols, which represent addition products of approximately 2-15 mol ethylene oxide and/or propylene oxide with fatty alcohols having 8 to 22 C atoms,
sulfated fatty acid alkylene glycol esters of formula (E1-II)

R$^7$CO(AlkO)$_n$SO$_3$M                    (E1-II), in which R$^7$CO— stands for a linear or branched, aliphatic, saturated and/or unsaturated acyl radical having 6 to 22 C atoms, Alk stands for CH$_2$CH$_2$, CHCH$_3$CH$_2$, and/or CH$_2$CHCH$_3$, n stands for numbers from 0.5 to 5, and M stands for a cation as described in German Unexamined Patent Application 197 36 906,
amide ether carboxylic acids,
condensation products of C$_8$-C$_{30}$ fatty alcohols with protein hydrolysates and/or amino acids and the derivatives thereof, which are known to those skilled in the art as protein fatty acid condensates, for example the Lamepon® types, Gluadin® types, and Hostapon® KCG or Amisoft® types.

Preferred anionic surfactants are alkyl sulfates, alkyl polyglycol ether sulfates, and ether carboxylic acids having 10 to 18 C atoms in the alkyl group and up to 12 glycol ether groups in the molecule, sulfosuccinic acid mono- and dialkyl esters having 8 to 18 C atoms in the alkyl group, and sulfosuccinic acid monoalkyl polyoxyethyl esters having 8 to 18 C atoms in the alkyl group and 1 to 6 oxyethyl groups, monoglyceride sulfates, alkyl and alkenyl ether phosphates, and protein fatty acid condensates.

Also usable according to the invention are cationic surfactants of the quaternary ammonium compound, esterquat, and amidoamine types. Preferred quaternary ammonium compounds are ammonium halides, in particular chlorides and bromides, such as alkyltrimethylammonium chlorides, dialkyldimethylammonium chlorides, and trialkylmethylammonium chlorides. The long alkyl chains of these surfactants preferably include 10 to 18 carbon atoms, such as in cetyl trimethylammonium chloride, stearyl trimethylammonium chloride, distearyl dimethylammonium chloride, lauryl dimethylammonium chloride, lauryl dimethylbenzylammonium chloride, and tricetyl methylammonium chloride, for example. Further preferred cationic surfactants are the imidazolium compounds known under the INCI names Quaternium-27 and Quaternium-83.

Surface-active compounds bearing at least one quaternary ammonium group and at least one —COO$^{(-)}$ or —SO$_3^{(-)}$ group in the molecule are referred to as zwitterionic surfactants. Particularly suitable zwitterionic surfactants are the so-called betaines, such as N-alkyl-N,N-dimethylammonium glycinates, for example coco alkyldimethylammonium glycinate, N-acylaminopropyl-N,N-dimethylammonium glycinates, for example coco acylaminopropyl dimethylammonium glycinate, and 2-alkyl-3-carboxymethyl-3-hydroxyethyl imidazolines, in each case having 8 to 18 C atoms in the alkyl or acyl group, and coco acylaminoethyl-hydroxyethylcarboxymethyl glycinate. A preferred zwitterionic surfactant is the fatty acid amide derivative known under the INCI name Cocamidopropyl Betaine.

Ampholytes are understood to mean surface-active compounds which, in addition to a C$_8$-C$_{24}$ alkyl or acyl group in the molecule, include at least one free amino group and at least one —COOH or —SO$_3$H group and are capable of forming internal salts. Examples of suitable ampholytes are N-alkyl glycines, N-alkylpropionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids, and alkylaminoacetic acids, in each case having approximately 8 to 24 C atoms in the alkyl group. Particularly preferred ampholytes are N-cocoalkylamino propionate, coco acylaminoethylamino propionate, and C$_{12}$-C$_{18}$ acyl sarcosine.

The agents used according to the invention can include the ingredients and active substances in a cosmetically acceptable carrier.

Preferred cosmetically acceptable carriers are aqueous, alcoholic, or aqueous-alcoholic media preferably including at least 10% by weight water, based on the overall agent. In particular the lower alcohols including 1 to 4 carbon atoms, for example ethanol and isopropanol, which are customarily used for cosmetic purposes may be included as alcohols.

It is preferred according to the invention to use at least one (C$_1$ to C$_4$) monoalkyl alcohol in the agents according to the invention, in particular in a quantity of 1 to 50% by weight, in particular 5 to 30% by weight. This is in turn preferred in particular for preparation as a pump foam or aerosol foam.

Organic solvents or a mixture of solvents having a boiling point below 400° C. may be included as additional co-solvents in a quantity of 0.1 to 15% by weight, preferably 1 to 10% by weight, based on the overall agent. Unbranched or branched hydrocarbons such as pentane, hexane, isopentane, and cyclic hydrocarbons such as cyclopentane and cyclohexane are particularly suited as additional co-solvents. Further particularly preferred water-soluble solvents are glycerin, ethylene glycol, and propylene glycol in a quantity of up to 30% by weight, based on the overall agent.

In particular the addition of glycerin and/or propylene glycol and/or polyethylene glycol and/or polypropylene glycol increases the flexibility of the polymer film that is formed when the agent according to the invention is applied. Thus, if a flexible hold is desired, the agents according to the invention preferably include 0.01 to 30% by weight of glycerin and/or propylene glycol and/or polyethylene glycol and/or polypropylene glycol, based on the overall agent.

The agents preferably have a pH of 6.8 to 9.5, in particular 7.0 to 8.5. Within the meaning of the present document, the statements regarding pH refer to the pH at 25° C., unless noted otherwise.

The agents used according to the invention may additionally include the auxiliary substances and additives which are customarily added to conventional styling products.

In particular, additional care substances are mentioned as suitable auxiliary substances and additives.

A silicone oil and/or a silicone gum, for example, may be used as a care substance.

Silicone oils or silicone gums which are suitable according to the invention are in particular dialkyl and alkylaryl siloxanes, for example dimethyl polysiloxane and methyl phenyl polysiloxane, and the alkoxylated, quaternized, or anionic derivatives thereof. Cyclic and linear polydialkyl siloxanes, the alkoxylated and/or aminated derivatives thereof, dihydroxy polydimethyl siloxanes, and polyphenyl alkyl siloxanes are preferred.

Silicone oils bring about a variety of effects. For example, they simultaneously influence dry and wet combability, the feel of dry and wet hair, and luster. The term "silicone oils" is understood by those skilled in the art to mean a plurality of structures of organosilicon compounds. These are primarily understood to be dimethiconols.

The following commercial products are mentioned as examples of these types of products: Botanisil NU-150M (Botanigenics), Dow Corning 1-1254 Fluid, Dow Corning 2-9023 Fluid, Dow Corning 2-9026 Fluid, Ultrapure Dimethiconol (Ultra Chemical), Unisil SF-R (Universal Preserve), X-21-5619 (Shin-Etsu Chemical Co.), Abil OSW 5 (Degussa Care Specialties), ACC DL-9430 Emulsion (Taylor Chemical Company), AEC Dimethiconol & Sodium Dodecylbenzenesulfonate (A & E Connock (Perfumery & Cosmetics) Ltd.), B C Dimethiconol Emulsion 95 (Basildon Chemical Company, Ltd.), Cosmetic Fluid 1401, Cosmetic Fluid 1403, Cosmetic Fluid 1501, Cosmetic Fluid 1401 DC (all from Chemsil Silicones, Inc.), Dow Corning 1401 Fluid, Dow Corning 1403 Fluid, Dow Corning 1501 Fluid, Dow Corning 1784 HVF Emulsion, Dow Corning 9546 Silicone Elastomer Blend (all from Dow Corning Corporation), Dub Gel SI 1400 (Stearinerie Dubois Fils), HVM 4852 Emulsion (Crompton Corporation), Jeesilc 6056 (Jeen International Corporation), Lubrasil, Lubrasil DS (both from Guardian Laboratories), Nonychosine E, Nonychosine V (both from Exsymol), San-Surf Petrolatum-25, Satin Finish (both from Collaborative Laboratories, Inc.), Silatex-D30 (Cosmetic Ingredient Resources), Silsoft 148, Silsoft E-50, Silsoft E-623 (all from Crompton Corporation), SM555, SM2725, SM2765, SM2785 (all from GE Silicones), Taylor T-Sil CD-1, Taylor TME-4050E (all from Taylor Chemical Company), THV 148 (Crompton Corporation), Tixogel CYD-1429 (Sud-Chemie Performance Additives), Wacker-Belsil CM 1000, Wacker-Belsil CM 3092, Wacker-Belsil CM 5040, Wacker-Belsil DM 3096, Wacker-Belsil DM 3112 VP, Wacker-Belsil DM 8005 VP, Wacker-Belsil DM 60081 VP (all from Wacker-Chemie GmbH).

Dimethicones constitute the second group of silicones which may be included according to the invention. These may be both linear and branched, as well as cyclic or cyclic and branched.

Dimethicone copolyols (S3) constitute a further group of suitable silicones. Such dimethicone copolyols are commercially available, and are marketed, for example, by Dow Corning under the name Dow Corning® 5330 Fluid.

The teaching according to the invention naturally also encompasses that the dimethiconols, dimethicones, and/or dimethicone copolymers may already be present as an emulsion. The corresponding emulsion of the dimethiconols, dimethicones, and/or dimethicone copolyols may be produced from the corresponding dimethiconols, dimethicones, and/or dimethicone copolyols after preparation of same, and by customary emulsification methods known to those skilled in the art. For this purpose, cationic, anionic, nonionic, or zwitterionic surfactants, and emulsifiers may be used as auxiliary substances as aids in producing the corresponding emulsions. Of course, the emulsions of the dimethiconols, dimethicones, and/or dimethicone copolyols may also be produced directly by an emulsion polymerization method. Such methods are also well known to those skilled in the art.

When the dimethiconols, dimethicones, and/or dimethicone copolyols are used as an emulsion, according to the invention the droplet size of the emulsified particles is 0.01 to 10,000 µm, preferably 0.01 to 100 µm, particularly preferably 0.01 to 20 µm, and very particularly preferably 0.01 to 10 µm. The particle size is determined according to the light scattering method.

When branched dimethiconols, dimethicones, and/or dimethicone copolyols are used, this is understood to mean that the degree of branching is greater than random branching which occurs by chance due to impurities in the particular monomers. Within the meaning of the present invention, branched dimethiconols, dimethicones, and/or dimethicone copolyols are therefore understood to mean that the degree of branching is greater than 0.01%. The degree of branching is preferably greater than 0.1%, very particularly preferably greater than 0.5%. The degree of branching is determined from the ratio of unbranched monomers to branching monomers, i.e., the quantity of tri- and tetrafunctional siloxanes. Slightly branched as well as highly branched dimethiconols, dimethicones, and/or dimethicone copolyols may be very particularly preferred according to the invention.

Aminofunctional silicones, in particular the silicones that are combined under the INCI name Amodimethicone, are particularly suitable silicones. It is therefore preferred according to the invention when the agents according to the invention additionally include at least one aminofunctional silicone. These are understood to be silicones which have at least one, optionally substituted, amino group. These silicones are designated as Amodimethicone according to the INCI declaration, and are obtainable, for example, in the form of an emulsion as the commercial product Dow Corning® 939 or as the commercial product Dow Corning® 949 in a mixture with a cationic surfactant and a nonionic surfactant.

Aminofunctional silicones which have an amine value above 0.25 meq/g, preferably above 0.3 meq/g, and particularly preferably above 0.4 meq/g, are preferably used. The amine value stands for the milliequivalents of amine per gram of the aminofunctional silicone. The amine value may be determined by titration, and is also expressed in the units mg KOH/g.

The agents preferably include the silicones in quantities of 0.01% by weight to 15% by weight, particularly preferably 0.05 to 2% by weight, based on the overall agent.

The agent may include, for example, at least one protein hydrolysate and/or one of the derivatives thereof as a care substance of a different compound class.

Protein hydrolysates are product mixtures which are obtained by the acidically, basically, or enzymatically catalyzed breakdown of proteins. According to the invention, the term "protein hydrolysates" is also understood to mean total hydrolysates as well as individual amino acids and the derivatives thereof, and mixtures of various amino acids. The molar weight of the protein hydrolysates which are usable according to the invention is between 75 Dalton, the molar weight of glycine, and 200,000 Dalton; the molar weight is preferably 75 to 50,000 Dalton, and very particularly preferably 75 to 20,000 Dalton.

Protein hydrolysates of plant, animal, or marine origin or of synthetic origin may be used according to the invention.

Examples of protein hydrolysates are elastin, collagen, keratin, silk, and milk protein hydrolysates, which may also be present in the form of salts. Such products are marketed, for example, under the trademarks Dehylan® (Cognis), Promois® (Interorgana), Collapuron® (Cognis), Nutrilan®

(Cognis), Gelita-Sol® (Deutsche Gelatine Fabriken Stoess & Co.), Lexein® (Inolex), Sericin (Pentapharm), and Kerasol® (Croda).

The protein hydrolysates are included in the agents according to the invention in concentrations, for example, of 0.01% by weight to 20% by weight, preferably 0.05% by weight to 15% by weight, and very particularly preferably in quantities of 0.05% by weight to 5% by weight, in each case based on the overall application preparation.

The agent according to the invention may also include at least one vitamin, a provitamin, a vitamin precursor, and/or one of the derivatives thereof as a care substance.

According to the invention, vitamins, provitamins, and vitamin precursors are preferred which are customarily associated with the groups A, B, C, E, F, and H.

The group of substances denoted as vitamin A includes retinol (vitamin $A_1$) and 3,4-didehydroretinol (vitamin $A_2$). β-Carotene is the provitamin of retinol. For example, vitamin A acid and the esters thereof, vitamin A aldehyde, and vitamin A alcohol and the esters thereof, such as the palmitate and the acetate, are suitable as the vitamin A component. The agents preferably include the vitamin A component in quantities of 0.05-1% by weight, based on the overall application preparation.

The vitamin B group or the vitamin B complex includes, among others, vitamin $B_1$ (thiamine), vitamin $B_2$ (riboflavin), vitamin $B_3$ (nicotinic acid and/or nicotinic acid amide (niacinamide)), vitamin Bs (pantothenic acid, panthenol, and pantolactone), vitamin $B_6$ (pyridoxine as well as pyridoxamine and pyridoxal), vitamin C (ascorbic acid), vitamin E (tocopherols, in particular α-tocopherol), vitamin F (linoleic acid and/or linolenic acid), and vitamin H.

The agents according to the invention preferably include vitamins, provitamins, and vitamin precursors from the groups A, B, C, E, and H. Panthenol, pantolactone, pyridoxine, and the derivatives thereof, as well as nicotinic acid amide and biotin, are particularly preferred.

D-Panthenol, optionally in combination with at least one of the above-mentioned silicone derivatives, is very particularly preferably used as a care substance.

The same as for the addition of glycerin and/or propylene glycol, the addition of panthenol increases the flexibility of the polymer film that is formed when the agent according to the invention is applied. Thus, if a particularly flexible hold is desired, the agents according to the invention may include panthenol instead of or in addition to glycerin and/or propylene glycol. In one preferred embodiment, the agents according to the invention include panthenol, preferably in a quantity of 0.05 to 10% by weight, particularly preferably 0.1 to 5% by weight, in each case based on the overall agent.

The agents used according to the invention may also include at least one plant extract as a care substance.

These extracts are customarily produced by extraction of the entire plant. However, in individual cases it may also be preferable to produce the extracts solely from flowers and/or leaves of the plant.

Primarily preferred according to the invention are extracts of green tea, oak bark, nettle, witch hazel, hops, henna, chamomile, burdock root, horsetail, hawthorn, lime blossom, almond, aloe vera, spruce needle, horse chestnut, sandalwood, juniper berry, coconut, mango, apricot, lemon, wheat, kiwi fruit, melon, orange, grapefruit, sage, rosemary, birch, mallow, cuckoo flower, wild thyme, yarrow, thyme, lemon balm, restharrow, coltsfoot, marsh mallow, meristem, *ginseng*, and ginger.

Furthermore, it may be preferable to use mixtures of a plurality of different plant extracts, in particular two, in the agents used according to the invention.

Mono- or oligosaccharides may also be used as a care substance in the agents according to the invention.

Monosaccharides as well as oligosaccharides, for example cane sugar, lactose, and raffinose, may be used. The use of monosaccharides is preferred according to the invention. Among the monosaccharides, in turn compounds which include 5 or 6 carbon atoms are preferred.

Examples of suitable pentoses and hexoses are ribose, arabinose, xylose, lyxose, allose, altrose, glucose, mannose, gulose, idose, galactose, talose, fucose, and fructose. Arabinose, glucose, galactose, and fructose are preferably used carbohydrates. Glucose, which is suitable both in the D (+) or L (−) configuration or as a racemate, is very particularly preferably used. In addition, derivatives of these pentoses and hexoses, such as the corresponding aldonic and uronic acids (saccharic acids), sugar alcohols, and glycosides, may also be used according to the invention. Preferred saccharic acids are gluconic acid, glucuronic acid, saccharic acid, mannosaccharic acid, and mucic acid. Preferred sugar alcohols are sorbite, mannite, and dulcite. Methylglucosides are preferred glycosides.

Since the mono- or oligosaccharides used are customarily obtained from natural raw materials such as starch, they generally have configurations corresponding to these raw materials (for example, D-glucose, D-fructose, and D-galactose).

The mono- or oligosaccharides are preferably included in the agents used according to the invention in a quantity of 0.1 to 8% by weight, particularly preferably 1 to 5% by weight, based on the overall application preparation.

The agent may also include at least one lipid as a care substance.

Lipids suitable according to the invention are phospholipids, for example soy lecithin, egg lecithin, and cephalins, and the substances known under the INCI names Linoleamidopropyl PG-Dimonium Chloride Phosphate, Cocamidopropyl PG-Dimonium Chloride Phosphate, and Stearamidopropyl PG-Dimonium Chloride Phosphate. These are marketed, for example, by Mona under the trade names Phospholipid EFA®, Phospholipid PTC®, and Phospholipid SV®. The agents according to the invention preferably include the lipids in quantities of 0.01 to 10% by weight, in particular 0.1 to 5% by weight, based on the overall application preparation.

It is preferred according to the invention, in particular when the agent according to the invention is formulated as a cream that the cosmetic agent according to the invention additionally includes at least one oil phase.

According to the invention, an oil phase is understood to mean a phase that is liquid at 20° C., and which has a solubility of less than 1 g in 100 g water at 20° C.

The oil phase preferably has a viscosity of up to 1000 mPas (Brookfield, RVDV II+, 20° C., 20 rpm, spindle No. 1).

In one preferred embodiment, the oil of the oil phase is selected from at least one oil of the group comprising plant oils, animal oils, ester oils, liquid fatty acids and/or their mono-, di-, and trifatty acid esters of saturated and/or unsaturated linear and/or branched $C_6$ to $C_{22}$ fatty acids with glycerin.

Preferred plant oils are selected from at least one representative of the group comprising amaranth oil, sunflower oil, olive oil, soybean oil, rapeseed oil, castor oil, sesame oil, almond oil, jojoba oil, orange oil, apricot kernel oil, macadamia nut oil, wheat germ oil, peach kernel oil, and the liquid components of coconut oil.

Preferred ester oils are selected from esters of $C_6$-$C_{30}$ fatty acids with $C_2$-$C_{30}$ fatty alcohols. The monoesters of fatty acids with alcohols having 2 to 24 C atoms are preferred. Examples of fatty acid components used in the esters are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaostearic acid, arachidonic acid, gadoleic acid, behenic acid, and erucic acid and the technical mixtures thereof which are obtained, for example, in the compressive cleavage of natural fats and oils, in the oxidation of aldehydes from Roelen's oxosynthesis, or in the dimerization of unsaturated fatty acids. Examples of the fatty alcohol components in the ester oils are isopropyl alcohol, caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinic alcohol, linolyl alcohol, linolenyl alcohol, eleostearyl alcohol, arachidyl alcohol, gadoleyl alcohol, behenyl alcohol, erucyl alcohol, and brassidyl alcohol, and the technical mixtures thereof which are obtained, for example, in the high-pressure hydrogenation of technical methyl esters based on fats and oils or aldehydes from Roelen's oxosynthesis, and as the monomer fraction in the dimerization of unsaturated fatty alcohols. Particularly preferred according to the invention are isopropyl myristate (Rilanit® IPM), isononanoic acid-C16-18 alkyl ester (Cetiol® SN), 2-ethylhexyl palmitate (Cegesoft® 24), stearic acid 2-ethylhexyl ester (Cetiol® 868), cetyl oleate, glycerin tricaprylate, coco fatty alcohol caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), and oleic acid decyl ester (Cetiol® V).

Mono-, di-, and trifatty acid esters of saturated and/or unsaturated linear and/or branched fatty acids with glycerin, preferably usable as oil in the oil phase, are in particular the triglyceride esters of capric acid and caprylic acid (INCI name: Caprylic/Capric Triglycerides), obtainable, for example, as a commercial product from Cognis under the name Myritol® 312.

The additional oil phase is preferably included in the agent according to the invention in a quantity of 0.05% by weight to 25% by weight, in particular 0.1% by weight to 20% by weight, in each case based on the weight of the cosmetic agent.

Moreover, agents according to the invention which additionally include at least one fat are suitable.

According to the invention, a fat is understood to mean compounds having a solubility of less than 1 g in 100 g water at 20°.

The fat is preferably selected from at least one fat of the group comprising candelilla wax, shea butter, carnauba wax, beeswax, coconut fat, and $C_{12}$ to $C_{20}$ fatty acids (in particular palmitic acid, stearic acid).

The additional fat is preferably included in the agent according to the invention in a quantity of 0.05% by weight to 35% by weight, in particular 1% by weight to 20% by weight, in each case based on the weight of the cosmetic agent.

If the agents according to the invention are present in the form of a cream or a gel, it is preferred according to the invention to additionally add at least one polymeric thickener. This thickener is different from the mentioned starches modified with propylene oxide. The thickeners may be selected, for example, from among the polymeric thickeners known under the following INCI names: Acrylamides Copolymer, Acrylamide/Sodium Acrylate Copolymer, Acrylamide/Sodium Acryloyldimethyltaurate Copolymer, Acrylates/Acetoacetoxyethyl Methacrylate Copolymer, Acrylates/Beheneth-25 Methacrylate Copolymer, Acrylates/C10-30 Alkyl Acrylate Crosspolymer, Acrylates/Ceteth-20 Itaconate Copolymer, Acrylates/Ceteth-20 Methacrylate Copolymer, Acrylates/Laureth-25 Methacrylate Copolymer, Acrylates/Palmeth-25 Acrylate Copolymer, Acrylates/Palmeth-25 Itaconate Copolymer, Acrylates/Steareth-50 Acrylate Copolymer, Acrylates/Steareth-20 Itaconate Copolymer, Acrylates/Steareth-20 Methacrylate Copolymer, Acrylates/Stearyl Methacrylate Copolymer, Acrylates/Vinyl Isodecanoate Crosspolymer, Acrylic Acid/Acrylonitrogens Copolymer, Agar, Agarose, Alcaligenes Polysaccharides, Algin, Alginic Acid, Ammonium Acrylates/Acrylonitrogens Copolymer, Ammonium Acrylates Copolymer, Ammonium Acryloyldimethyltaurate/Vinyl Formamide Copolymer, Ammonium Acryloyldimethyltaurate/VP Copolymer, Ammonium Alginate, Ammonium Polyacryloyldimethyl Taurate, Amylopectin, Ascorbyl Methylsilanol Pectinate, *Astragalus Gummifer* Gum, Attapulgite, *Avena Sativa* (Oat) Kernel Flour, Bentonite, Butoxy Chitosan, *Caesalpinia Spinosa* Gum, Calcium Alginate, Calcium Carboxymethyl Cellulose, Calcium Carrageenan, Calcium Potassium Carbomer, Calcium Starch Octenylsuccinate, C20-40 Alkyl Stearate, Carbomer, Carboxybutyl Chitosan, Carboxymethyl Chitin, Carboxymethyl Chitosan, Carboxymethyl Dextran, Carboxymethyl Hydroxyethylcellulose, Carboxymethyl Hydroxypropyl Guar, Cellulose Acetate Propionate Carboxylate, Cellulose Gum, *Ceratonia Siliqua* Gum, Cetyl Hydroxyethylcellulose, Cholesterol/HDI/Pullulan Copolymer, Cholesteryl Hexyl Dicarbamate Pullulan, *Cyamopsis Tetragonoloba* (Guar) Gum, Diglycol/CHDM/Isophthalates/SIP Copolymer, Dihydrogenated Tallow Benzylmonium Hectorite, Dimethicone Crosspolymer-2, Dimethicone Propyl PG-Betaine, DMAPA Acrylates/Acrylic Acid/Acrylonitrogens Copolymer, Ethylene/Sodium Acrylate Copolymer, Gelatin, Gellan Gum, Glyceryl Alginate, *Glycine Soja* (Soybean) Flour, Guar Hydroxypropyltrimonium Chloride, Hectorite, Hydrated Silica, Hydrogenated Potato Starch, Hydroxybutyl Methylcellulose, Hydroxyethyl Acrylate/Sodium Acryloyldimethyl Taurate Copolymer, Hydroxyethylcellulose, Hydroxyethyl Chitosan, Hydroxyethyl Ethylcellulose, Hydroxypropylcellulose, Hydroxypropyl Chitosan, Hydroxypropyl Ethylenediamine Carbomer, Hydroxypropyl Guar, Hydroxypropyl Methylcellulose, Hydroxypropyl Methylcellulose Stearoxy Ether, Hydroxystearamide MEA, Isobutylene/Sodium Maleate Copolymer, Lithium Magnesium Silicate, Lithium Magnesium Sodium Silicate, *Macrocystis Pyrifera* (Kelp), Magnesium Alginate, Magnesium Aluminum Silicate, Magnesium Silicate, Magnesium Trisilicate, Methoxy PEG-22/Dodecyl Glycol Copolymer, Methylcellulose, Methyl Ethylcellulose, Methyl Hydroxyethylcellulose, Microcrystalline Cellulose, Montmorillonite, Moroccan Lava Clay, Natto Gum, Nonoxynyl Hydroxyethylcellulose, Octadecene/MA Copolymer, Pectin, PEG-800, PEG-Crosspolymer, PEG-150/Decyl Alcohol/SMDI Copolymer, PEG-175 Diisostearate, PEG-190 Distearate, PEG-15 Glyceryl Tristearate, PEG-140 Glyceryl Tristearate, PEG-240/HDI Copolymer Bis-Decyltetradeceth-20 Ether, PEG-100/IPDI Copolymer, PEG-180/Laureth-50/TMMG Copolymer, PEG-10/Lauryl Dimethicone Crosspolymer, PEG-15/Lauryl Dimethicone Crosspolymer, PEG-2M, PEG-5M, PEG-7M, PEG-9M, PEG-14M, PEG-20M, PEG-23M, PEG-25M, PEG-45M, PEG-65M, PEG-90M, PEG-115M, PEG-160M, PEG-120 Methyl Glucose Trioleate, PEG-180/Octoxynol- 40/TMMG Copolymer, PEG-150 Pentaerythrityl Tetrastearate, PEG-4 Rapeseedamide, PEG-150/Stearyl Alcohol/SMDI Copolymer, Polyacrylate-3, Polyacrylic Acid, Polycyclopentadiene, Polyether-1, Polyethylene/Isopropyl Maleate/MA Copolyol, Polymethacrylic Acid, Polyquaternium-52, Polyvinyl Alcohol, Potassium Alginate, Potassium Aluminum Polyacrylate, Potassium Carbomer, Potassium Carrageenan, Potassium Polyacrylate, Potato Starch Modified, PPG-14 Laureth-60 Hexyl Dicarbamate, PPG-14 Laureth-60 Isophoryl Dicarbamate, PPG-14 Palmeth-60 Hexyl Dicarbamate, Propylene Glycol Alginate, PVP/Decene Copolymer, PVP Montmorillonite, Rhizobian Gum, Ricinoleic Acid/Adipic Acid/AEEA Copolymer, Sclerotium Gum, Sodium Acrylate/Acryloyldimethyl Taurate Copolymer, Sodium Acrylates/Acrolein Copolymer, Sodium Acrylates/Acrylonitrogens Copolymer, Sodium Acrylates Copolymer, Sodium Acrylates/Vinyl Isodecanoate Crosspolymer, Sodium Acrylate/Vinyl Alcohol Copolymer, Sodium Carbomer, Sodium Carboxymethyl Chitin, Sodium Carboxymethyl Dextran, Sodium Carboxymethyl Beta-Glucan, Sodium Carboxymethyl Starch, Sodium Carrageenan, Sodium Cellulose Sulfate, Sodium Cyclodextrin Sulfate, Sodium Hydroxypropyl Starch Phosphate, Sodium Isooctylene/MA Copolymer, Sodium Magnesium Fluorosilicate, Sodium Polyacrylate, Sodium Polyacrylate Starch, Sodium Polyacryloyldimethyl Taurate, Sodium Polymethacrylate, Sodium Polystyrene Sulfonate, Sodium Silicoaluminate, Sodium Starch Octenylsuccinate, Sodium Stearoxy PG-Hydroxyethylcellulose Sulfonate, Sodium Styrene/Acrylates Copolymer, Sodium Tauride Acrylates/Acrylic Acid/Acrylonitrogens Copolymer, *Solanum Tuberosum* (Potato) Starch, Starch/Acrylates/Acrylamide Copolymer, Starch Hydroxypropyltrimonium Chloride, Steareth-60 Cetyl Ether, Steareth-100/PEG-136/HDI Copolymer, *Sterculia Urens* Gum, Synthetic Fluorphlogopite, *Tamarindus Indica* Seed Gum, Tapioca Starch, TEA-Alginate, TEA-Carbomer, *Triticum Vulgare* (Wheat) Starch, Tromethamine Acrylates/Acrylonitrogens Copolymer, Tromethamine Magnesium Aluminum Silicate, Welan Gum, Yeast Beta-Glucan, Yeast Polysaccharides, *Zea Mays* (Corn) Starch.

The polymeric thickener is particularly preferably selected from among polymeric, anionic, amphiphilic thickeners, particularly preferably among those with the INCI names Acrylates/Beheneth-25 Methacrylate Copolymer, Acrylates/C10-30 Alkyl Acrylate Crosspolymer, Acrylates/Ceteth-20 Itaconate Copolymer, Acrylates/Ceteth-20 Methacrylate Copolymer, Acrylates/Laureth-25 Methacrylate Copolymer, Acrylates/Palmeth-20 Acrylate Copolymer, Acrylates/Palmeth-25 Acrylate Copolymer, Acrylates/Palmeth-25 Itaconate Copolymer, Acrylates/Steareth-50 Acrylate Copolymer, Acrylates/Steareth-20 Itaconate Copolymer, Acrylates/Steareth-20 Methacrylate Copolymer, Acrylates/Stearyl Methacrylate Copolymer, Acrylates/Vinyl Isodecanoate Crosspolymer, Acrylates/Steareth-20 Methacrylate Crosspolymer.

The polymeric thickeners are preferably included in the agent according to the invention in a quantity of 0.5 to 20% by weight, in particular 0.5 to 10% by weight, in cream form or gel form. According to the invention, this is preferably a transparent gel.

Although any of the mentioned care substances alone already provides a satisfactory result, within the scope of the present invention, all embodiments are also encompassed in which the agent also includes a plurality of care substances from various groups.

The agents themselves as well as the treated fibers may be protected from harmful effects of UV radiation by adding a UV filter. Therefore, at least one UV filter is preferably added to the agent. Suitable UV filters are not subject to general restrictions with regard to their structure and their physical properties. Rather, all UV filters which are usable in the cosmetics sector, having an absorption maximum in the UVA range (315-400 nm), in the UVB range (280-315 nm), or in the UVC range (<280 nm) are suitable. UV filters having an absorption maximum in the UVB range, in particular in the range of approximately 280 to approximately 300 nm, are particularly preferred.

The UV filters preferred according to the invention may be selected, for example, from substituted benzophenones, p-aminobenzoic acid esters, diphenylacrylic acid esters, cinnamic acid esters, salicylic acid esters, benzimidazoles, and o-aminobenzoic acid esters.

Examples of UV filters that are usable according to the invention are 4-aminobenzoic acid, N,N,N-trimethyl-4-(2-oxobom-3-ylidene methyl)aniline methyl sulfate, 3,3,5-trimethylcyclohexyl salicylate (homosalate), 2-hydroxy-4-methoxybenzophenone, 2-phenylbenzimidazole-5-sulfonic acid and the potassium, sodium, and triethanolamine salts thereof, 3,3'-(1,4-phenylenedimethylene)-bis(7,7-dimethyl-2-oxo-bicyclo-[2.2.1]hept-1-yl-methanesulfonic acid) and the salts thereof, 1-(4-tert-butylphenyl)-3-(4-methoxyphenyl)propane-1,3-dione, α-(2-oxoborn-3-ylidene)toluene-4-sulfonic acid and the salts thereof, ethoxylated 4-aminobenzoic acid ethyl ester (PEG-25 PABA; Uvinul®P 25), 4-dimethylaminobenzoic acid 2-ethylhexyl ester, salicylic acid 2-ethylhexyl ester, 4-methoxycinnamic acid isopentyl ester, 4-methoxycinnamic acid 2-ethylhexyl ester, 2-hydroxy-4-methoxybenzophenone-5-sulfonic acid and the sodium salt thereof (benzophenone-4; Uvinul®MS 40; Uvasorb®S 5), 3-(4'-methylbenzylidene)-D,L-camphor, 3-benzylidene camphor, 4-isopropylbenzyl salicylate, 2,4,6-trianilino-(p-carbo-2'-ethylhexyl-1'-oxy)-1,3,5-triazine, 3-imidazol-4-yl acrylic acid and the ethyl ester thereof, polymers of N-{(2 and 4)-[2-oxoborn-3-ylidene methyl]benzyl}acrylamide, 2,4-dihydroxybenzophenone, 1,1'-diphenylacrylonitrilic acid 2-ethylhexyl ester, o-aminobenzoic acid menthyl ester, 2,2',4,4'-tetrahydroxybenzophenone, 2,2'-dihydroxy-4,4'-dimethoxybenzophenone, 2,2'-dihydroxy-4,4'-dimethoxybenzophenone-5-sodium sulfonate, and 2-cyano-3,3-diphenylacrylic acid 2'-ethylhexyl ester. 2-Hydroxy-4-methoxybenzophenone-5-sulfonic acid and the sodium salt thereof and/or ethoxylated 4-aminobenzoic acid ethyl ester are preferred.

The UV filters are customarily included in quantities of 0.01-5% by weight, based on the overall application preparation. Quantities of 0.1-2.5% by weight are preferred.

In one particular embodiment, the agent used according to the invention also includes one or more direct dyes. This allows the treated keratinic fiber to not only be temporarily structured, but at the same time also dyed when the agent is applied. This may be desirable in particular when only a temporary coloration, for example with striking fashionable colors, is desired which may be removed from the keratinic fiber simply by washing.

Direct dyes are customarily nitrophenylenediamines, nitroaminophenols, azo dyes, anthraquinones, or indophenols. Preferred direct dyes are the compounds known under the international names or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 11, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52, as well as 1,4-diamino-2-nitrobenzene, 2-amino-4-nitrophenol, 1,4-bis-(β-hydroxyethyl)amino-2-nitrobenzene, 3-nitro-4-β-hydroxyethyl)aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid, and 2-chloro-6-ethylamino-1-hydroxy-4-nitrobenzene. Cationic direct dyes are preferably used. In this regard, particularly preferred are (a) cationic triphenylmethane dyes, for example Basic Blue 7, Basic Blue 26, Basic Violet 2, and Basic Violet 14,
(b) aromatic systems that are substituted with a quaternary nitrogen group, for example Basic Yellow 57, Basic Red 76, Basic Blue 99, Basic Brown 16, and Basic Brown 17, and
(c) direct dyes that include a heterocycle which has at least one quaternary nitrogen atom, as mentioned, for example, in Claims 6 to 11 in EP-A2-998 908, to which explicit reference is made at this point.

The dyes that are also known under the names Basic Yellow 87, Basic Orange 31, and Basic Red 51 are very particularly preferably cationic direct dyes of group (c). The cationic direct dyes, marketed under the trademark Arianor®, are cationic direct dyes which likewise are very particularly preferred according to the invention.

According to this embodiment, the agents used according to the invention preferably include the direct dyes in a quantity of 0.001 to 20% by weight, based on the overall agent.

It is preferred according to the invention that the agents used according to the invention are free of oxidation dye precursors. Oxidation dye precursors are divided into so-called developer components and coupler components. The developer components form the actual dyes with one another under the influence of oxidizing agents or atmospheric oxygen, or by coupling with one or more coupler components.

The agents used according to the invention preferably are provided as a pump spray or aerosol spray, but preferably as a pump foam or aerosol foam.

For this purpose, the agents according to the invention are provided in a dispensing device which is either a compressed gas container ("aerosol container") that is additionally filled with a propellant, or a non-aerosol container.

The compressed gas containers, by means of which a product is dispersed via a valve due to the internal gas pressure in the container, are referred to by definition as "aerosol containers". As the converse of the aerosol container definition, a "non-aerosol container" is a container under standard pressure, by means of which a product is dispersed through a pump system via mechanical action.

The agents used according to the invention are particularly preferably provided as an aerosol hair foam or aerosol hairspray. The agent according to the invention therefore preferably additionally includes at least one propellant.

Propellants that are suitable according to the invention are selected, for example, from $N_2O$, dimethyl ether, $CO_2$, air, alkanes having 3 to 5 carbon atoms, such as propane, n-butane, isobutane, n-pentane, and isopentane, and the mixtures thereof. Dimethyl ether, propane, n-butane, isobutane, and mixtures thereof are preferred.

According to one preferred embodiment, the mentioned alkanes, mixtures of the mentioned alkanes, or mixtures of the mentioned alkanes with dimethyl ether are used as the sole propellant. However, the invention also expressly encompasses the joint use of propellants of the chlorofluorocarbon type, but in particular fluorocarbons.

For a given spray device, the sizes of the aerosol droplets or of the foam bubbles and the respective size distribution may be adjusted via the quantity ratio of propellant to the other components of the preparations.

The quantity of propellant used varies depending on the specific composition of the agent, the packaging used, and the desired product type, such as hairspray or hair foam. When conventional spray devices are used, aerosol foam products preferably include the propellant in quantities of 1 to 35% by weight, based on the overall product. Quantities of 2 to 30% by weight, in particular 3 to 15% by weight, are particularly preferred. Aerosol sprays generally include larger quantities of propellant. In this case, the propellant is preferably used in a quantity of 30 to 98% by weight, based on the overall product. Quantities of 40 to 95% by weight, in particular 50 to 95% by weight, are particularly preferred.

The aerosol products may be produced in the customary manner. All components of the particular agent, with the exception of the propellant, are generally filled into a suitable pressure-resistant container. The container is then closed with a valve. Lastly, the desired quantity of propellant is filled, using conventional techniques.

Isopentane is preferably suitable as a propellant for expansion of agents in gel form in a two-chamber aerosol container, and is incorporated into the agents according to the invention and provided in the first chamber of the two-chamber aerosol container. At least one further propellant which is different from isopentane, and which builds up a higher pressure than isopentane in the two-chamber aerosol container, is provided in the second chamber of the two-chamber aerosol container. The propellants of the second chamber are preferably selected from $N_2O$, dimethyl ether, $CO_2$, air, alkanes having 3 or 4 carbon atoms (such as propane, n-butane, isobutane), and mixtures thereof.

The use according to the invention of the above-described agents allows an improvement of the color retention of oxidatively dyed keratinic fibers.

A further subject matter of the present patent application relates to a method for treating keratin-containing fibers, in particular human hair, comprising the following steps:
i) carrying out oxidative dyeing of the keratin-containing fiber,
ii) applying an agent which includes in a cosmetically acceptable carrier
a) at least one copolymer A comprising at least one structural unit (A1), at least one structural unit (A2), at least one structural unit (A3), and at least one structural unit (A4)

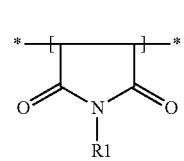

(A1)

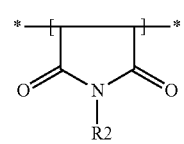

(A2)

-continued

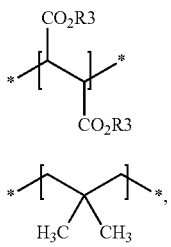

wherein
- R1 stands for an optionally heterofunctionalized alkyl radical;
- R2 stands for an optionally heterofunctionalized alkyl radical which is different from R1;
- R3 independently stands for an optionally heterofunctionalized alkyl radical which is different from R1 and R2;

b) at least one copolymer B, which is different from copolymer A, having at least one structural unit (B1)

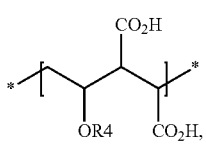

wherein R4 stands for an optionally heterofunctionalized alkyl radical, to the oxidatively dyed keratin-containing fiber.

The above-mentioned preferred embodiments of copolymers A and B and of the dispensing devices (see above) are considered preferred according to the invention.

In one preferred embodiment of the method according to the invention, the agent is applied to the keratin-containing fibers and the keratin-containing fibers are shaped in step ii). This shape is fixed by the agent applied in step ii).

EXAMPLES

The following quantity statements are in percent by weight, unless noted otherwise.

The following formulations were provided by mixing the stated raw materials:

| Raw materials | E1 | V1 |
|---|---|---|
| Styleze XT3[1] | 10.0 | — |
| Amphomer 028-4910[2] | — | 2.7 |
| 2-Amino-2-methylpropan-1-ol | — | 0.50 |
| Water | ad 100 | |

[1]INCI: Water (and) Polyimide-1 (and) PVM/MA Copolymer (and) Caprylyl Glycol (27% by weight active content of the polymer; Akzo)
[2]Octylacrylamide/Acrylates/Butylaminoethylmethacrylate Copolymer (Akzo)

After application to oxidatively dyed keratinic fibers, formulation E1 brought about improved color retention, compared to formulation V1, after numerous hair washings.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. Method for treating keratin-containing fibers, in particular human hair, comprising the following steps:
   i) carrying out oxidative dyeing of the keratin-containing fiber,
   ii) applying an agent to the oxidatively dyed keratin-containing fiber, said agent including a cosmetically acceptable carrier and
   a) at least one copolymer A comprising at least one structural unit (A1), at least one structural unit (A2), at least one structural unit (A3), and at least one structural unit (A4)

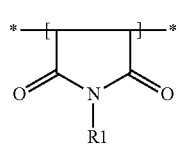

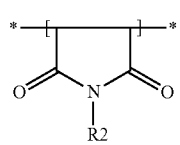

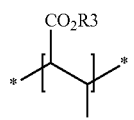

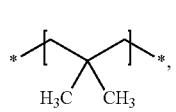

wherein
- R1 stands for an optionally heterofunctionalized alkyl radical;
- R2 stands for an optionally heterofunctionalized alkyl radical which is different from R1;
- R3 independently stands for an optionally heterofunctionalized alkyl radical which is different from R1 and R2;

b) at least one copolymer B, which is different from copolymer A, having at least one structural unit (B1)

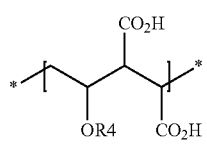

wherein R4 stands for an optionally heterofunctionalized alkyl radical.

2. The method of claim 1, improves the color retention of the oxidatively dyed keratin-containing fibers.

3. The method of claim 1, wherein R1 in formula (A1) stands for a $-CH(CH_3)CH_2-(OCH(CH_3)CH_2)_x(O[CH_2]_2)_y OCH_3$ radical, in which x and y independently have a value between 1 and 100.

4. The method of claim 1, wherein the radical R2 in the structural unit (A2) stands for a radical containing an amino group.

5. The method of claim 4, wherein the amino group is a tertiary amine.

6. The method of claim 1, wherein at least one of the radicals R3 of the structural unit (A3) stands for an alkyl radical.

7. The method of claim 6, wherein the alkyl radical is a C1 to C4 alkyl radical.

8. The method of claim 1, wherein the radical R4 in the structural unit (B1) stands for an alkyl radical.

9. The method of claim 8, wherein the alkyl radical is a C1 to C4 alkyl radical.

10. The method of claim 8, wherein the alkyl radical is $-CH_3$.

11. The method of claim 1, wherein the weight fraction of copolymer A relative to the total weight of cosmetic agents according to the invention is 0.05 to 10% by weight.

12. The method of claim 1, wherein the weight fraction of copolymer A relative to total weight of cosmetic agents according to the invention is 0.2 to 5.0% by weight.

13. The method of claim 1, wherein the weight fraction of copolymer B relative to the total weight of cosmetic agents according to the invention is 0.05 to 10% by weight.

14. The method of claim 1, wherein the weight fraction of copolymer B relative to the total weight of cosmetic agents according to the invention is 0.2 to 5.0% by weight.

15. The method of claim 1, wherein the weight ratio of copolymer A to copolymer B is 20:1 to 1:20.

16. The method of claim 1, wherein the weight ratio of copolymer A to copolymer B is 5:1 to 1:5.

17. The method of claim 1, wherein the total quantity of the mixture of copolymer A and copolymer B is 0.1 to 10.0%, based on the total weight of the agent.

18. The method of claim 1, wherein the total quantity of the mixture of copolymer A and copolymer B is 1.0 to 5.0% by weight, based on the total weight of the agent.

19. The method of claim 1, wherein the agent has a pH of 6.8 to 9.5.

20. The method of claim 1, wherein the agent is present as a cream, gel, pump foam, or aerosol foam.

* * * * *